US009189574B2

(12) United States Patent
Looney et al.

(10) Patent No.: US 9,189,574 B2
(45) Date of Patent: Nov. 17, 2015

(54) COMPUTER BASED MODELS OF HOOK AND LOOP FASTENING SYSTEMS

(71) Applicant: The Procter & Gamble Company, Cincinnati, OH (US)

(72) Inventors: Michael Timothy Looney, Blue Ash, OH (US); Nayda Liz Ramosmedina, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 379 days.

(21) Appl. No.: 13/787,878

(22) Filed: Mar. 7, 2013

(65) Prior Publication Data
US 2013/0246013 A1 Sep. 19, 2013

Related U.S. Application Data

(60) Provisional application No. 61/610,120, filed on Mar. 13, 2012.

(51) Int. Cl.
*G06F 17/50* (2006.01)
*A61F 13/49* (2006.01)
*A61F 13/56* (2006.01)

(52) U.S. Cl.
CPC ...... *G06F 17/5009* (2013.01); *A61F 13/49014* (2013.01); *A61F 13/5638* (2013.01)

(58) Field of Classification Search
USPC ............... 703/2; 604/361, 385.29, 391, 386; 428/99
See application file for complete search history.

(56) References Cited

U.S. PATENT DOCUMENTS

| | | | |
|---|---|---|---|
| 4,579,537 A * | 4/1986 | Leahy | 446/100 |
| 6,810,300 B1 | 10/2004 | Woltman et al. | |
| 7,099,734 B2 | 8/2006 | Pieper et al. | |
| 7,373,284 B2 | 5/2008 | Stabelfeldt et al. | |
| 8,747,379 B2 * | 6/2014 | Fletcher et al. | 604/389 |
| 2009/0076783 A1 | 3/2009 | Babusik et al. | |
| 2010/0121293 A1 * | 5/2010 | Fletcher et al. | 604/361 |
| 2014/0200542 A1 * | 7/2014 | Magee | A61F 13/49007 604/385.25 |
| 2014/0200543 A1 * | 7/2014 | Chatterjee | A61F 13/49014 604/386 |

OTHER PUBLICATIONS

"Smart Attachment Mechanism", Joseph William Clement, pp. 1-271, 2004.
"Design and analysis of novel hook and loop fastening system", Richard Edward Dooley, M.S. Eng., pp. 1-79, 1991.

* cited by examiner

*Primary Examiner* — Thai Phan
(74) *Attorney, Agent, or Firm* — Christian M. Best

(57) ABSTRACT

Methods of modeling hook and loop fastening systems are disclosed.

41 Claims, 8 Drawing Sheets

COMPUTER BASED MODELS OF HOOK AND LOOP FASTENING SYSTEMS

CROSS REFERENCE TO RELATED APPLICATION

This application claims priority under 35 U.S.C. §119(e) to U.S. Provisional Patent Application Ser. No. 61/610,120, filed on Mar. 13, 2012, the entire disclosure of which is hereby incorporated by reference.

FIELD

In general, embodiments of the present disclosure relate to hook and loop fastening systems. In particular, embodiments of the present disclosure relate to methods of modeling hook and loop fastening systems with hook materials having a plurality of male fastening elements and with loop materials having a plurality of female fastening elements.

BACKGROUND

A hook and loop fastening system can be used to fasten things together. For example, a hook and loop fastening system can be used to fasten a disposable wearable absorbent article around a wearer. In a hook and loop fastening system, a male fastening material includes male fastening elements, such as hooks, and a female fastening material includes female fastening elements, such as loops. The male fastening material and the female fastening material are configured to releasably engage with each other. If the elements of the fastening materials are not well designed, then few of the elements effectively engage, and the materials cannot be used to form a reliable hook and loop fastening system. It can be difficult to predict which fastening materials can be used to form a reliable hook and loop fastening system.

SUMMARY

However, embodiments of the present disclosure can at least assist in predicting whether or not particular male fastening materials and/or particular female fastening materials can be used to form reliable hook and loop fastening systems. The present disclosure includes methods of simulating the physical behavior of hook and loop fastening systems. As a result, fastening materials, fastening systems, and articles with fastening systems can be evaluated and modified as computer based models before they are tested as real world things.

DETAILED DESCRIPTION

Figure 1:
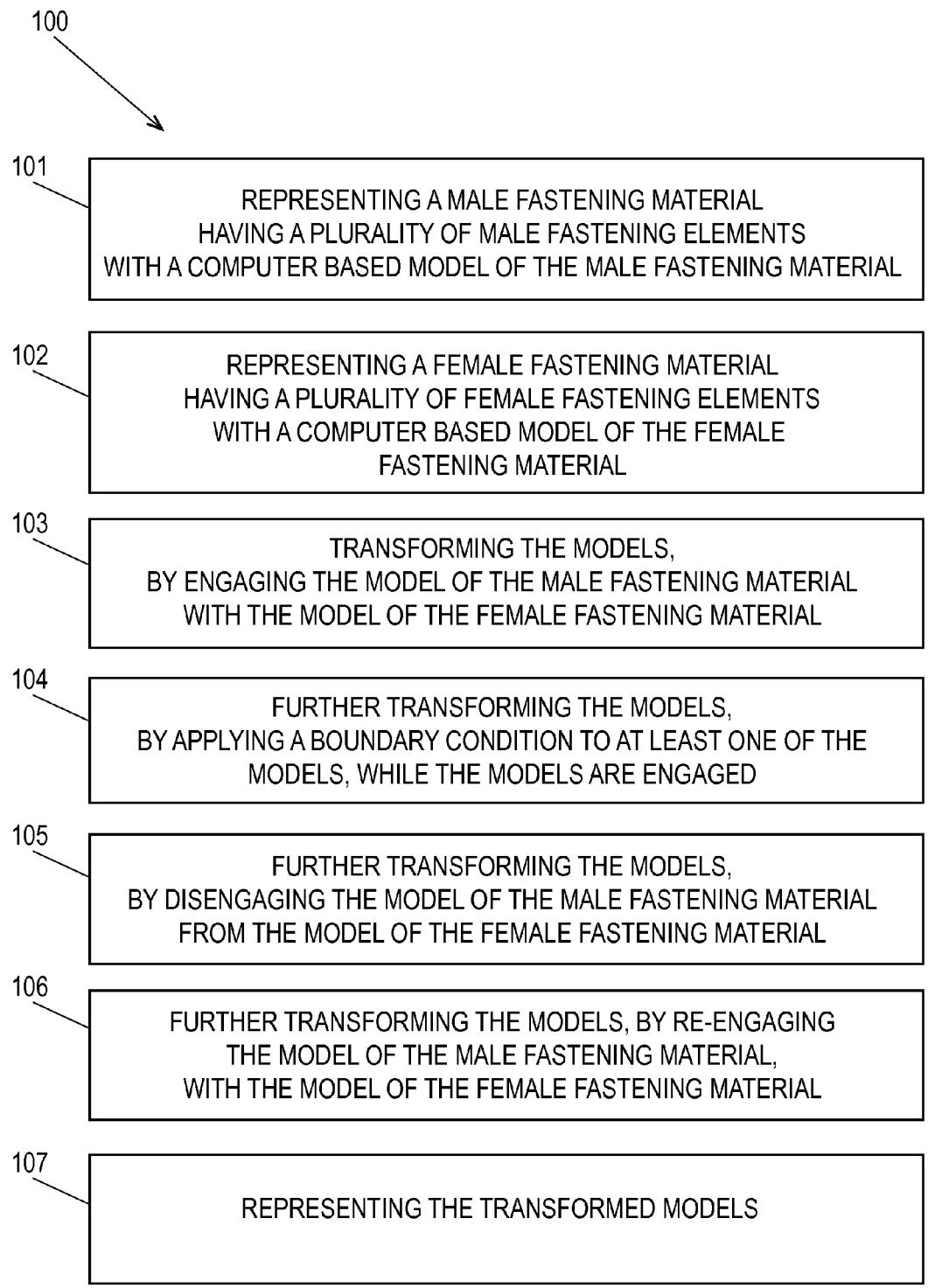
FIG. 1 is a chart illustrating a method of using computer based models for simulating the physical behavior of fastening materials in hook and loop fastening systems.

Embodiments of the present disclosure can at least assist in predicting whether or not particular male fastening materials and/or particular female fastening materials can be used to form reliable hook and loop fastening systems. The present disclosure includes methods of simulating the physical behavior of hook and loop fastening systems. As a result, fastening materials, fastening systems, and articles with fastening systems can be evaluated and modified as computer based models before they are tested as real world things.

Computer aided engineering (CAE) is a broad area of applied science in which technologists use software to develop computer based models that represent real world things. The models can be transformed to provide various information about the physical behavior of those real world things, under certain conditions and/or over particular periods of time. With CAE, the interactions of the computer based models are referred to as simulations. Sometimes the real world things are referred to as a problem and the computer based model is referred to as a solution.

Finite element analysis (FEA) is a major category of CAE. In FEA, models representing mechanical things, as well as their features, components, structures, and/or materials are transformed to predict stress, strain, displacement, deformation, and other mechanical behaviors. FEA represents a solid material as a set of discrete elements. In FEA, the mechanical behavior of each element is calculated, using equations that describe mechanical behavior. The results of all of the elements are summed up, to represent the mechanical behavior of the material as a whole.

Commercially available software can be used to conduct CAE. Abaqus, from SIMULIA in Providence, R.I., and LSDyna from Livermore Software Technology Corp. in Livermore, Calif., are examples of commercially available FEA software. CAE software can be run on various computer hardware, such as a personal computer, a minicomputer, a cluster of computers, a mainframe, a supercomputer, or any other kind of machine on which program instructions can execute to perform CAE functions.

CAE software can represent a number of real world things, such as absorbent articles. An absorbent article can receive, contain, and absorb bodily exudates (e.g. urine, menses, feces, etc.). Absorbent articles include products for sanitary protection, for hygienic use, and the like. Some absorbent articles are wearable. A wearable absorbent article is configured to be worn on or around a lower torso of a body of a wearer. Examples of wearable absorbent articles include diapers and incontinence undergarments. Some absorbent articles are disposable. A disposable absorbent article is configured to be disposed of after a single use (e.g., not intended to be reused, restored, or laundered). Examples of disposable absorbent articles include disposable diapers, disposable incontinence undergarments, as well as feminine care pads and liners. Some absorbent articles are reusable. A reusable absorbent article is configured to be partly or wholly used more than once. A reusable absorbent article is configured such that part or all of the absorbent article is durable, or wear-resistant to laundering, or fully launderable. An example of a reusable absorbent article is a diaper with a washable outer cover. CAE can be used to design, simulate, and/or evaluate all kinds of absorbent articles, their features, materials, structures, and compositions, as well as their performance characteristics.

CAE software can also represent components of a hook and loop fastening system, such as a male fastening material and a female fastening material. A hook and loop fastening system can be used to fasten things together. For example, a hook and loop fastening system can be used to fasten a disposable wearable absorbent article around a wearer. In a hook and loop fastening system, a male fastening material includes male fastening elements, such as hooks, and a female fastening material includes female fastening elements, such as loops. The male fastening material and the female fastening material are configured to releasably engage with each other.

FIG. 1 is a chart illustrating a method 100 of steps 101-107 for using computer based models for simulating the physical behavior of materials in hook and loop fastening systems. Although the steps 101-107 are described in numerical order in the present disclosure, in various embodiments some or all of these steps can be performed in other orders, and/or at overlapping times, and/or at the same time, as will be understood by one of ordinary skill in the art.

The method 100 includes a first step 101 of representing a male fastening material having a plurality of male fastening elements, with a computer based model. The model of the male fastening material can be created as described in connection with the embodiments of FIG. 2. In various embodiments, the model of the male fastening material can include part, parts, or all of a male fastening material as described in connection with the embodiments of FIG. 2. For example, the model may include the hooks but not the substrate of a male fastening material. As an alternate example, the model may include just one or two hooks. As a further example, the model may include part or parts of male fastening elements (e.g. for a hook with a cap and stem, just the cap can be modeled) but not all of the male fastening elements of a male fastening material. In the first step 101, the model may represent a male fastening material, which has a defined size and a particular shape representing a size and a shape of a discrete piece of male fastening material in a hook and loop fastening system.

The method 100 includes a second step 102 of representing a female fastening material having a plurality of female fastening elements, with a computer based model. The model of the female fastening material can be created as described in connection with the embodiments of FIG. 3. In various embodiments, the model of the female fastening material can include part, parts, or all of a female fastening material as described in connection with the embodiments of FIG. 3. As an alternate example, the model may include just one or two fiber loops. As another example, the model may include part or parts of female fastening elements (e.g. partial fiber segments) but not all of the female fastening elements of a female fastening material. In the second step 102, the model may represent a female fastening material, which has a defined size and a particular shape representing a size and a shape of a discrete piece of female fastening material in a hook and loop fastening system.

The method 100 includes a third step 103 of transforming the models from the first step 101 and from the second step 102 by simulating an engaging of the model of the male fastening material from the first step 101 with the model of the female fastening material from the second step 102, to form engaged fastening materials. The transforming of the third step 103 can be performed by using CAE software, such as FEA. The transforming of the third step 103 includes a mechanical interaction between the model of the male fastening material from the first step 101 with the model of the female fastening material from the second step 102. Prior to or during the third step 103, these models can be brought into the same modeling space.

In the engaging simulated in the third step 103, FEA program instructions can execute to bring the models together, by moving either or both of the model of the male fastening material from the first step 101 and the model of the female fastening material from the second step 102. In one embodiment, the models can be engaged by moving the model of the male fastening material into contact with the model of the female fastening material, while the model of the female fastening material remains stationary with respect to the model of the male fastening material. In another embodiment, the models can be engaged by moving the model of the female fastening material into contact with the model of the male fastening material, while the model of the male fastening material remains stationary. In still another embodiment, the models can be engaged by moving the model of the male fastening material while also moving the model of the female fastening material, to bring the models into contact with each other.

In the engaging simulated in the third step 103, FEA program instructions can execute to bring the models together, by moving either or both of the model of the male fastening material from the first step 101 and the model of the female fastening material from the second step 102, horizontally, vertically, or both horizontally and vertically, with respect to each other. In one embodiment, the models can be engaged by moving the model of the male fastening material only vertically into contact with the model of the female fastening material, while the model of the female fastening material remains stationary. In another embodiment, the models can be engaged by moving the model of the male fastening material only horizontally into contact with the model of the female fastening material, while the model of the female fastening material remains stationary. In still another embodiment, the models can be engaged by moving the model of the male fastening material both horizontally and vertically into contact with the model of the female fastening material, while the model of the female fastening material remains stationary. In variations of these embodiments, the simulations can be reversed such that the model of the female fastening material can be the moving material while the model of the male fastening material remains stationary. In further variations of these embodiments, simulations can be combined, such that any embodiment of moving the model of the male fastening material can be combined with any embodiment of moving the model of the female fastening material. These movements are further described in connection with the embodiments of FIG. 4A.

The engaging simulated in the third step 103 may also result in some deformation and/or breakage of part, parts, or all of the model of the male fastening material from the first step 101 and/or part, parts, or all of the model of the female fastening material from the second step 102. As an example, the simulation may result in the deforming (e.g. bending) of at least some, or substantially all, or even all of the male fastening elements, or part, parts, or all of the male fastening material. As another example, the simulation may result in the deforming (e.g. deflection) of at least some, or substantially all, or even all of the female fastening elements, or part, parts, or all of the female fastening material.

In the engaging simulated in the third step 103, FEA program instructions can execute to simulate the mechanical interaction between the model of the male fastening material from the first step 101 and the model of the female fastening material from the second step 102. However, the present disclosure contemplates that, in an alternate embodiment, part, or parts, or all of the third step 103 can be performed using another kind of computer based program instructions, as will be understood by one of skill in the art. The simulation of the third step 103 transforms the model of the male fastening material from the first step 101 and with the model of the female fastening material from the second step 102 to form a computer based model that represents the fastening materials in an engaged configuration. There are various degrees of engagement, from partial engagement to full engagement, and the simulation of the third step 103 can transform the models of the fastening materials to represent any degree of engagement.

In some embodiments, the engaging simulated in the third step 103 can be performed until the model of the male fastening material from the first step 101 is at least partially engaged with the model of the female fastening material from the second step 102. In some embodiments, the engaging simulated in the third step 103 can be performed until the model of the male fastening material from the first step 101 is fully engaged with the model of the female fastening material from the second step 102. This fully engaged configuration is further described in connection with the embodiment of FIG. 4B.

For a computer based model with an article that includes a hook and loop fastening system having the model of the male fastening material from the first step 101 and the model of the female fastening material from the second step 102, the engaging of the third step 103 can be a fastening together of a first portion of the article to which the male fastening material is joined, and a second portion of the article to which the female fastening material is joined. For example, the engaging can be a fastening together of the fastening materials of a hook and loop fastening system in a fastenable wearable absorbent article, as described in connection with the embodiments of FIGS. 5A-6B. For a computer based model with a wearable absorbent article that includes a hook and loop fastening system, the engaging simulated in the third step 103 results in a model that can represent the fastened absorbent article such that the article is formed for wearing around a lower torso of the human body. This simulation may or may not include simulating a fitting of the wearable absorbent article to a computer based model of a human body. In various embodiments of such simulations, the model of the article can include part of the article, parts of the article, or all of the article.

The transforming simulated in the third step 103 involves the use of boundary conditions. Boundary conditions are defined variables that represent physical factors acting within a computer based model. Examples of boundary conditions include forces, pressures, velocities, and other physical factors. Each boundary condition can be assigned a particular magnitude, direction, and location within the model. These values can be determined by observing, measuring, analyzing, and/or estimating real world physical factors. In various embodiments, computer based models can also include one or more boundary conditions that differ from real world physical factors, in order to account for inherent limitations in the models and/or to more accurately represent the overall physical behaviors of real world things, as will be understood by one of ordinary skill in the art. Boundary conditions can act on the model in various ways, to move, constrain, and/or deform one or more parts in the model.

The method 100 includes an optional fourth step 104 of transforming the models from the first step 101 and from the second step 102 by applying one or more boundary conditions to either or both of the model of the male fastening material from the first step 101 and/or the model of the female fastening material from the second step 102, while the models are in the engaged configuration, resulting from the simulation of the third step 103. These boundary conditions can be used to simulate in use conditions for the engaged fastening materials.

The transforming of the fourth step 104 can be performed by using CAE software, such as FEA. The transforming of the fourth step 104 includes a mechanical interaction between the model of the male fastening material from the first step 101 and the model of the female fastening material from the second step 102.

The transforming of the fourth step 104 may also result in some deformation and/or breakage of part, parts, or all of the model of the male fastening material from the first step 101 and/or part, parts, or all of the model of the female fastening material from the second step 102. As an example, the transforming may result in the deforming (e.g. bending) of at least some, or substantially all, or even all of the male fastening elements, or part, parts, or all of the male fastening material. As another example, the transforming may result in the deforming (e.g. deflection) of at least some, or substantially all, or even all of the female fastening elements, or part, parts, or all of the female fastening material.

In the application of one or more boundary conditions simulated in the fourth step 104, FEA program instructions can execute to apply a peel force, a shear force, both a peel force and a shear force, or any other kind of loading condition, applied as one or more forces, displacements, or other boundary conditions, or any combinations of any of these, to either or both of the model of the male fastening material from the first step 101 and the model of the female fastening material from the second step 102, while the models are engaged with each other. These one or more boundary conditions can be used to simulate the real world conditions in which the fastening system would perform. In one embodiment, a peel force can be applied to the model of the male fastening material, while the model of the female fastening material remains stationary, as described in connection with the embodiment of FIG. 4C. Alternatively, this simulation can be reversed such that the peel force can be applied to the model of the female fastening material, while the model of the male fastening material remains stationary. Additionally, these simulations can be combined, such that a peel force can be applied to the model of the male fastening material, while another peel force is applied to the model of the female fastening material.

In another embodiment, a shear force can be applied to the model of the male fastening material, while the model of the female fastening material remains stationary. Alternatively, this simulation can be reversed such that the shear force can be applied to the model of the female fastening material, while the model of the male fastening material remains stationary. Additionally, these simulations can be combined, such that a shear force can be applied to the model of the male fastening material, while another shear force is applied to the model of the female fastening material, as described in connection with the embodiment of FIG. 4D.

In further variations of these embodiments, simulations can be combined, such that any embodiment of peeling and/or shearing the model of the male fastening material can be combined with any embodiment of peeling and/or shearing the model of the female fastening material.

For a computer based model with an article that includes a hook and loop fastening system having the model of the male fastening material from the first step 101 and the model of the female fastening material from the second step 102, the application of the boundary condition(s) of the fourth step 104 can be used to simulate the real world conditions in which the fastening system would perform. For a computer based model with a wearable absorbent article that includes a hook and loop fastening system, the simulation of the fourth step 104 can result in a model that represents the fastened absorbent article experiencing in-use conditions from when the article is being worn around a lower torso of the human body.

In various embodiments of the method 100, the fourth step 104 can be omitted.

The method 100 includes an optional fifth step 105 of transforming the models from the first step 101 and from the second step 102 by disengaging the model of the male fastening material of the first step 101 from the model of the female fastening material of the second step 102. In one embodiment, wherein the fourth step 104 is included in the method 100, the fifth step can be performed while the models are or after the models have been subjected to the simulation of the fourth step 104. In another embodiment, wherein the fourth step 104 is omitted from the method 100, the fifth step can be performed while the models of the fastening materials are in an engaged configuration, resulting from the simulation of the third step 103.

The transforming of the fifth step 105 can be performed by using CAE software, such as FEA. The transforming of the fifth step 105 includes a mechanical interaction between the model of the male fastening material from the first step 101 and the model of the female fastening material from the second step 102.

In the disengaging simulated in the fifth step 105, FEA program instructions can execute to apply one or more actions of peeling, shearing, or any other kind of separating, applied as one or more forces, displacements, or boundary conditions, or any combinations of any of these to either or both of the model of the male fastening material from the first step 101 and the model of the female fastening material from the second step 102, while the models are at least partially engaged with each other. For example, any of the boundary conditions described in connection with the fourth step 104, can be used to disengage the model of the male fastening material from the model of the female fastening material. There are various degrees of disengagement, from partial disengagement to full disengagement, and the simulation of the fifth step 105 can transform the models of the fastening materials to represent any degree of disengagement.

In some embodiments, the disengaging simulated in the fifth step 105 can be performed until the model of the male fastening material from the first step 101 is at least partially disengaged from the model of the female fastening material from the second step 102. In some embodiments, the disengaging simulated in the fifth step 105 can be performed until the model of the male fastening material from the first step 101 is fully disengaged from the model of the female fastening material from the second step 102.

The disengaging simulated in the fifth step 105 may also result in some deformation and/or breakage of part, parts, or all of the model of the male fastening material from the first step 101 and/or of part, parts, or all of the model of the female fastening material from the second step 102. As an example, the simulation may result in the deforming (e.g. bending) of at least some of the male fastening elements. As another example, the simulation may result in the breaking (e.g. stretching beyond their ultimate tensile strength) of at least some of the female fastening elements.

For a computer based model with an article that includes a hook and loop fastening system having the model of the male fastening material from the first step 101 and the model of the female fastening material from the second step 102, the disengaging of the fifth step 105 can be used to simulate the unfastening of the fastening system. For a computer based model with a wearable absorbent article that includes a hook and loop fastening system, the disengaging simulated in the fifth step 105 can result in a model that represents the unfastening of the absorbent article when the article is being opened to be checked by a wearer or caregiver or when the article is being removed from the wearer, or even unintentional unfastening resulting from in-use conditions, environmental conditions, etc.

In various embodiments of the method 100, the fifth step 105 can be omitted.

The method 100 includes an optional sixth step 106 of transforming the models from the first step 101 and from the second step 102 by simulating a re-engaging of the model of the male fastening material from the first step 101 with the model of the female fastening material from the second step 102, after the models of the fastening materials have been at least partially disengaged, resulting from the simulation of the fifth step 105. In some embodiments, the transforming of the sixth step 106 can be performed on fastening materials that have been only partially disengaged. In other embodiments, the transforming of the sixth step 106 can be performed on fastening materials that have been fully disengaged. The transforming of the sixth step 106 can be performed by using CAE software, such as FEA.

The transforming of the sixth step 106 includes a mechanical interaction between the model of the male fastening material from the first step 101 and the model of the female fastening material from the second step 102. Prior to or during the sixth step 106, these models can be disengaged from each other. In the re-engaging simulated in the sixth step 106, FEA program instructions can execute to bring the models of the fastening material together, in any of the ways described in connection with the third step 103.

For a computer based model with an article that includes a hook and loop fastening system having the model of the male fastening material from the first step 101 and the model of the female fastening material from the second step 102, the re-engaging of the sixth step 106 can be used to simulate the refastening of the fastening system. For a computer based model with a wearable absorbent article that includes a hook and loop fastening system, the re-engaging simulated in the sixth step 106 can result in a model that represents the refastening of the absorbent article when the article is being closed after being checked by a wearer or caregiver or when the article is being fitted back onto a wearer after being removed.

In various embodiments of the method 100, the sixth step 106 can be omitted.

The method 100 includes a seventh step 107 of representing the transformed models of the fastening materials. In various embodiments, the representing of the seventh step 107 can be performed multiple times during the method 100.

In an embodiment of the method 100, where the fourth step 104, the fifth step 105, and the sixth step 106 are omitted, the representing of the seventh step 107 can be representing the results of the third step 103, that is, representing the transformed fastening materials with a computer based model of the engaged fastening materials.

In an embodiment of the method 100, where the fourth step 104 is included, but the fifth step 105 and the sixth step 106 are omitted, the representing of the seventh step 107 can be representing the results of the fourth step 104, that is, representing the further transformed fastening materials with a computer based model of the engaged fastening materials, subjected to one or more boundary conditions.

In an embodiment of the method 100, where the fifth step 105 is included, but the sixth step 106 is omitted, the representing of the seventh step 107 can be representing the results of the fifth step 105, that is, representing the further transformed fastening materials with a computer based model of at least partially disengaged, or even fully disengaged, fastening materials; this embodiment may or may not include the fourth step 104.

In an embodiment of the method 100, where the fifth step 105 and the sixth step 106 are included, the representing of the seventh step 107 can be representing the results of the sixth step 106, that is, representing the further transformed fastening materials with a computer based model of at least partially re-engaged, or even fully re-engaged, fastening materials; this embodiment may or may not include the fourth step 104.

After the seventh step 107 is completed, the method can be ended or the method can be extended by repeating one or more of the previous steps. As an example, in some embodiments, after the sixth step 106 is completed, the fourth step 104 and (optionally) the seventh step 107 can be repeated, for any number of times. As another example, in some embodiments, after the sixth step 106 is completed, the fourth step 104 and the fifth step 105 and (optionally) the seventh step 107 can be repeated, for any number of times. As a further example, in some embodiments, after the sixth step 106 is completed, the fourth step 104, and the fifth step 105, and the sixth step 106 and (optionally) the seventh step 107 can be repeated, for any number of times. As an example, in some embodiments, after the seventh step 107 is completed, the fourth step 104 and (optionally) the seventh step 107 can be repeated, for any number of times. As another example, in some embodiments, after the seventh step 107 is completed, the fourth step 104 and the fifth step 105 and (optionally) the seventh step 107 can be repeated, for any number of times. As another example, in some embodiments, after the seventh step 107 is completed, the fourth step 104, and the fifth step 105, and the sixth step 106 and (optionally) the seventh step 107 can be repeated, for any number of times.

By following repeating embodiments, such as those described above, the method 100 can be used to simulate multiple instances of fastening, loading, unfastening, and/or re-fastening, for a hook and loop fastening system. In the real world, some hook and loop fastening systems are often fastened, loaded, unfastened, and/or re-fastened multiple times. As a result, by simulating multiple fastening cycles, the method 100 can be used to accurately represent the real-world use of such hook and loop fastening systems, including the use of such systems in articles such as wearable absorbent articles.

In some embodiments of the method 100, one or more environmental objects and/or environmental conditions can physically interact with part, or parts, or all of the model of the male fastening material of the first step 101, with part, or parts, or all of the model of the female fastening material of the second step 102, and/or with part, or parts, or all of the model of an article that includes either or both fastening materials, as described herein. Such environmental objects and/or environmental conditions can physically interact with any or all of the models during one or more of any of the steps of the method 100.

Figure 2:
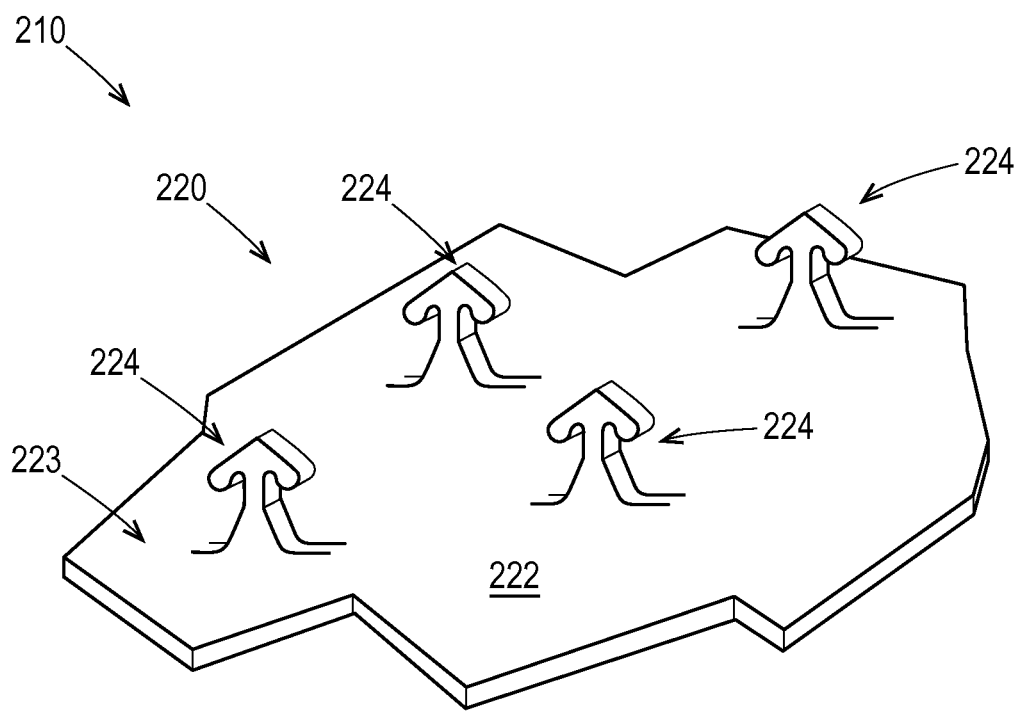
FIG. 2 is a representation of a computer based model of an exemplary male fastening material, suitable for use in a hook and loop fastening system, shown in an isometric view.

FIG. 2 is a representation of a computer based model 210 of an exemplary male fastening material 220, suitable for use in a hook and loop fastening system. A male fastening material has male fastening elements (e.g. hooks), which are protrusions configured to capture corresponding female fastening elements (e.g. loops). However, embodiments of the present disclosure can use any kind of male fastening material. FIG. 2 shows an isometric view of the top of the male fastening material 220. The male fastening material 220 includes a plurality of male fastening elements 224 disposed on a substrate 222 that has an overall planar shape. However, in various embodiments, a substrate for a male fastening material may not be planar, either due to a curved design or deformation from its original shape. Each of the male fastening elements 224 is configured as a bidirectional micro-sized hook, however, in various embodiments, one or more male fastening elements can be configured in any way, such as unidirectional, multidirectional, etc.

In the embodiment of FIG. 2, the male fastening elements 224 and the substrate 222 are made from the same material, and the male fastening elements 224 are a unified part of the substrate 222. The male fastening material 220 can be made from a wide variety of shapable and/or formable materials, including any natural or synthetic materials known in the art. Exemplary synthetic materials include but are not limited to polyolefins (e.g. polyethylene, polypropylene, polybutylene and the like); polyamides (e.g. nylon 6, nylon 6/6, nylon 10, nylon 12 and the like); polyesters (e.g. polyethylene terephthalate, polybutylene terephthalate, polylactic acid and the like); polycarbonate; polystyrene; thermoplastic elastomers; vinyl polymers; polyurethane; as well as blends and copolymers thereof, and any additives or processing aids known in the art. As a particular example, the male fastening material 220 can be made from various renewable materials. In various alternate embodiments, the male fastening elements and the substrate may be formed separately, or made from different materials.

The male fastening elements 224 can be distributed across the male fastening material 220 in various patterns and element densities. For example, the male fastening elements 224 can be arranged in rows and/or columns, or any other arrangement known in the art. In various embodiments, the male fastening material 220 can have an element density of 10-1,000 male fastening elements per square centimeter, or any integer number of male fastening elements between 10 and 1,000, or any range formed by any of these values. In various embodiments, the male fastening material 220 can be configured such that each male fastening element has an overall height of 1-1,000 micrometers, or any integer number between 10 and 1,000, or any range formed by any of these values.

Following are examples of male fastening materials suitable for use in a hook and loop fastening system. A male fastening material can include any number of hooks having any shape such as a "J" shape, a "T" shape, or a mushroom shape, or any other shape known in the art. In various embodiments, one male fastening material can include multiple hooks having differing shapes. Exemplary male fastening materials are available from Aplix, Inc. of Charlotte, N.C., USA under the trade designation 960, 957, and 942. Other male fastening materials are available from the 3M Company of St. Paul, Minn., USA under the trade designations CS200, CS300, MC5, and MC6. Still other male fastening materials are described in U.S. Pat. No. 5,058,247 entitled "Mechanical Fastening Prong" issued to Thomas Oct. 22, 1991, which is hereby incorporated by reference.

The male fastening material 220 and the male fastening elements 224 thereon can be made by any suitable process known in the art. For example, the male fastening material 220 can be made by casting, molding, profile extrusion, or microreplication. Further, the male fastening material 220 can be made by using any process described in any of the following U.S. Pat. Nos. 3,192,589; 3,138,841; 3,266,113; 3,408,705; 3,557,413; 3,594,863; 3,594,865; 3,718,725; 3,762,000; 4,001,366; 4,056,593; 4,189,809: 4,290,174; 4,454,183; 4,894,060; 5,077,870; 5,315,740; 5,607,635; 5,679,302; 5,879,604; 5,845,375; 6,054,091; 6,206,679; 6,209,177; 6,248,419; 6,357,088; 6,481,063; 6,484,371; 6,526,633; 6,635,212; 6,660,202; 6,728,998; 6,737,147; 6,869,554; RE38,652; 6,982,055; 7,014,906; 7,048,818; 7,032,278; 7,052,636; 7,052,638; 7,067,185; 7,172,008; 7,182,992; 7,185,401; 7,188,396; and 7,516,524, each of which is hereby incorporated by reference.

In another alternate embodiment, male fastening elements may be joined together to form a male fastening material without a substrate that has an overall planar shape. For example, a male fastening material can be made from a plurality of male fastening elements that are disposed on one or more strips of material, or disposed on one or more strands of material, or male fastening elements that are joined together to form one or more strips or one or more strands of material, or male fastening elements that are connected to one or more other common elements, in any manner known in the art.

A computer based model of a male fastening material, such as the computer based model 210 of the male fastening material 220 of FIG. 2, can be created in various ways, such as those described below. A computer based model that represents a male fastening material can be created by providing dimensions and material properties to modeling software and by generating a mesh for the male fastening elements using meshing software.

A computer based model of a male fastening material can be created with dimensions that are similar to or the same as dimensions that represent a real world male fastening material. These dimensions can be determined by measuring actual samples, by using known values, or by estimating values. Alternatively, a model of a male fastening material can be configured with dimensions that do not represent a real world male fastening material. For example, a model of a male fastening material can represent a new variation of a male fastening material or can represent an entirely new male fastening material. In these examples, dimensions for the model can be determined by varying actual or known values, by estimating values, or by generating new values. The model can be created by putting values for the dimensions of parts of the male fastening material into the modeling software.

The computer based model of the male fastening material can be created with material properties that are similar to or the same as material properties that represent a real world male fastening material. These material properties can be determined by measuring actual samples, by using known values, or by estimating values. Alternatively, a model of a male fastening material can be configured with material properties that do not represent a real world male fastening material. For example, a model of a male fastening material can represent a new variation of a real world male fastening material or can represent an entirely new male fastening material. In these examples, material properties for the model can be determined by varying actual or known values, by estimating values, or by generating new values.

The computer based model of the male fastening material can be created with a mesh for the parts of the male fastening elements. A mesh is a collection of small, connected geometric shapes that define the set of discrete elements in a CAD and/or FEA and/or CAE computer based model. The type of mesh and/or the size of elements can be controlled with user inputs into the meshing software, as will be understood by one of ordinary skill in the art. Each computer based model of a male fastening material, in the present disclosure, can be created in these ways.

Figure 3:
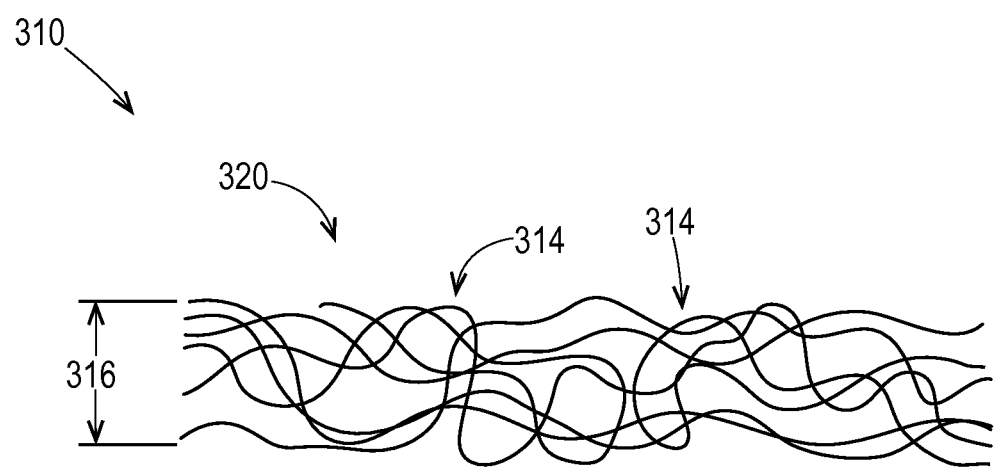
FIG. 3 is a representation of a computer based model of an exemplary female fastening material, suitable for use in a hook and loop fastening system, shown in a side view.

FIG. 3 is a representation of a computer based model 310 of an exemplary female fastening material 320, suitable for use in a hook and loop fastening system, shown in a side view. A female fastening material has female fastening elements (e.g. loops), which are configured to be captured by corresponding male fastening elements (e.g. hooks). The female fastening material 320 is a fibrous material with an overall thickness 316. In the embodiment of FIG. 3, the female fastening material 320 is a nonwoven material. The nonwoven material has a plurality of fibers 314.

The fibers 314 form fiber loops and each fiber loop has a fiber cross-section with an overall dimension (e.g. for a round fiber, the overall dimension of the cross-section is its diameter). The fibers 314 in the female fastening material 320 can have a cross-section with a uniform overall dimension, or a cross-section with an overall dimension that varies along the length of the fiber segment. In various embodiments, a fiber can have a cross-section with a different overall shape, such as oval, flat, tri-lobal, multi-lobal, etc.

In various embodiments, the female fastening material 320 can be any fibrous material or any other material suitable for releasably engaging hooks of a male fastening material, as disclosed herein or as known in the art. As an example, the fibrous outer surface of an outer cover of a disposable wearable absorbent article can be used as a female fastening material. In some embodiments, the female fastening material 320 can be disposed on a layer of material that acts as a substrate. In various embodiments, the female fastening material 320 can include any combination of any number or any kind of fibers (produced by any method), including fibers of varying size, shape, material, and configuration, as described herein, or as known in the art.

Fibrous materials can be made from one or more of various types of fibers, such as animal fibers, plant fibers, mineral fibers, synthetic fibers, etc. Fibrous materials can include short fiber, long fibers, continuous fibers, and/or fibers of varying lengths or combinations of any of these. In some cases, a fibrous material can include another material, can be joined to another material, or can be incorporated into another material. Fibrous materials can take many forms, such as fabrics, textiles, and composites. Examples of fabrics include fibrous textiles (woven or knitted fabrics), felts, nonwovens, and others. An example of a fibrous composite is a composite material with polymeric fibers.

Throughout the present disclosure, nonwoven materials are used to describe and illustrate various embodiments. However, it is contemplated that embodiments of the present disclosure are not limited to nonwoven materials, but can be similarly applied to a wide variety of fibrous materials, such as those described above and others, as will be understood by one of skill in the art. As used herein, the term "nonwoven material" refers to a sheet-like structure (e.g. web) of fibers (sometimes referred to as filaments) that are interlaid in a non-uniform, irregular, or random manner. A nonwoven material can be a single layer structure or a multiple layer structure. Each layer in a nonwoven material can include one kind of fibers or two or more kinds of fibers, with each kind of fiber configured in any way described herein or known in the art. A nonwoven material can also be joined to another material, such as a film, to form a laminate. A nonwoven web can be bonded to provide integrity to the web and/or to attach the nonwoven web to another material.

A nonwoven material can be made from various natural and/or synthetic materials. Exemplary natural materials include cellulosic fibers, such as cotton, jute, pulp, and the like; and also can include reprocessed cellulosic fibers like rayon or viscose. Natural fibers for a nonwoven material can be prepared using various processes such as carding. Notably, a nonwoven material can be made from fibers made from renewable materials. Exemplary synthetic materials include but are not limited to synthetic thermoplastic polymers that are known to form fibers, which include, but are not limited to, polyolefins (e.g. polyethylene, polypropylene, polybutylene and the like); polyamides (e.g. nylon 6, nylon 6/6, nylon 10, nylon 12 and the like); polyesters (e.g. polyethylene terephthalate, polybutylene terephthalate, polylactic acid and the like); polycarbonate; polystyrene; thermoplastic elastomers; vinyl polymers; polyurethane; as well as blends and copolymers thereof, and any additives or processing aids known in the art. Any of these materials can be used to form one or more mono-component fibers, and any combination of any of these materials can be used to form one or more of any kind of multi-component fibers in any configuration.

Fibers of a relatively short length (e.g. 40 mm or less) are typically manufactured into a nonwoven using processes like drylaying (e.g. carding or airlaying) or wetlaying. Continuous fibers or filaments can be spun out of molten thermoplastics or chemical solutions and formed into a web using spunlaying/spunbonding, meltblowing, or electrospinning by example. Another process for forming a nonwoven is film fibrillation. These processes can also be combined to form composite or layered fabric structures.

Each layer in a fibrous material or particular fibers in a fibrous material can be configured with various appropriate properties, such as air permeability, porosity, breathability, extensibility, elasticity, opacity, transparency, strength, and/or softness, etc. in any way known in the art.

In various embodiments, the overall thickness 316 can be 1-10,000 micrometers, or any integer value for micrometers between 1 and 10,000, or any range formed by any of these values. As examples, the overall thickness can be 350, 500, or 650 micrometers or any range formed by any of these values. The basis weight of the female fastening material 320 can be 10-100 grams per square meter, or any integer value for grams per square meter between 10 and 100, or any range formed by any of these values.

A computer based model of a female fastening material, such as the computer based model 310 of the female fastening material 320 of FIG. 3, can be created in various ways, such as those described below. A computer based model that represents a female fastening material can be created by providing dimensions and material properties to modeling software and by generating a mesh for the fiber using meshing software.

A computer based model of a female fastening material can be created with dimensions that are similar to or the same as dimensions that represent a real world female fastening material. These dimensions can be determined by measuring actual samples, by using known values, or by estimating values. Alternatively, a model of a female fastening material can be configured with dimensions that do not represent a real world female fastening material. For example, a model of a female fastening material can represent a new variation of a female fastening material or can represent an entirely new female fastening material. In these examples, dimensions for the model can be determined by varying actual or known values, by estimating values, or by generating new values. The model can be created by putting values for the dimensions of parts of the female fastening material into the modeling software. The model can represent a female fastening material created in various ways, such as by needle-punching, hydro-entangling, etc. As an example, a computer based model of a female fastening material can be a computer based model of a three-dimensional fibrous web, such as the models described in: U.S. patent application Ser. No. 13/029,154, entitled "Computer Based Models of Fibrous Materials"; U.S. patent application Ser. No. 13/029,157, entitled "Computer Based Models of Processed Fibrous Materials"; and U.S. provisional patent application Ser. No. 61/539,174, entitled "Computer Based Models of Three-Dimensional Fibrous Webs", each of which is hereby incorporated by reference.

The computer based model of the female fastening material can be created with material properties that are similar to or the same as material properties that represent a real world female fastening material. These material properties can be determined by measuring actual samples, by using known values, or by estimating values. Alternatively, a model of a female fastening material can be configured with material properties that do not represent a real world female fastening material. For example, a model of a female fastening material can represent a new variation of a real world female fastening material or can represent an entirely new female fastening material. In these examples, material properties for the model can be determined by varying actual or known values, by estimating values, or by generating new values.

The computer based model of the female fastening material can be created with a mesh for the parts of the fiber, as described above for the male fastening material. Each computer based model of a female fastening material, in the present disclosure, can be created in these ways.

As described above, male fastening materials and female fastening materials are described as separate materials, however, in various alternate embodiments, a single piece of material can have a portion configured as a male fastening material, and a portion configured as a female fastening material, or a single piece of material can include both male fastening elements and female fastening elements, or a single piece of material can include a single type of fastening element, which can function as both a male fastening element and as a female fastening element (such that a fastening material with this single type of fastening element can releasably engage with a male fastening material, a female fastening material, or another piece of fastening material configured in the same way). It is contemplated that methods of the present disclosure can include computer based models that can represent fastening materials configured according to any of these alternate embodiments.

Figure 4A:
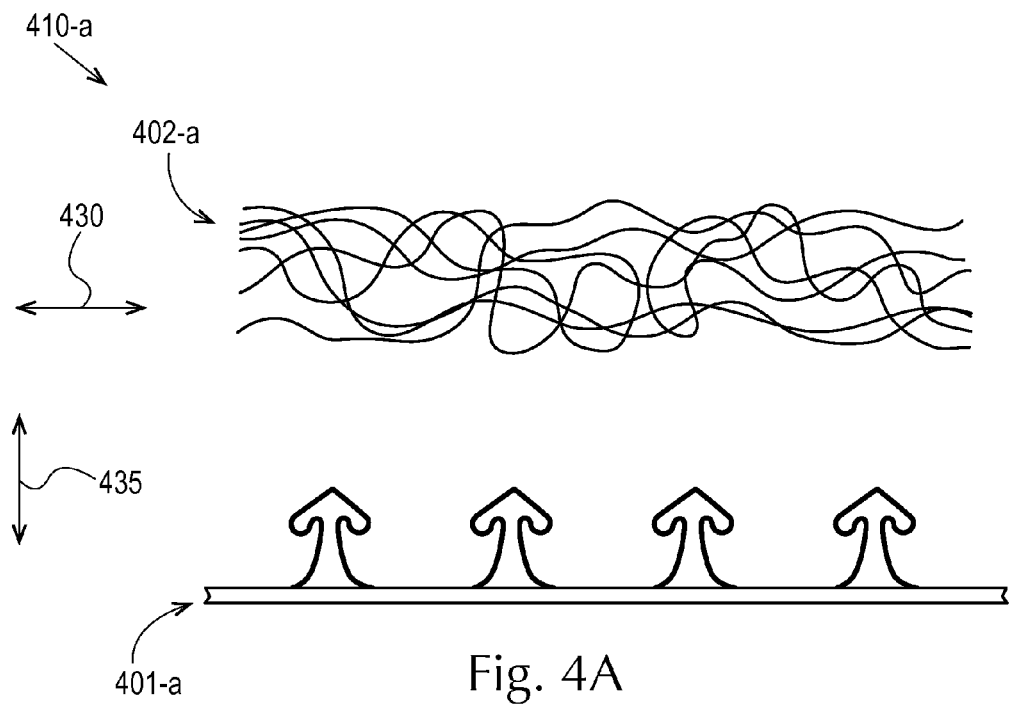
FIG. 4A is a representation of a computer based model of a male fastening material and a computer based model of a female fastening material, wherein the fastening materials are not yet engaged, shown in a side view.

FIG. 4A is a representation of a computer based model 410-*a* of a male fastening material 401-*a* and a female fastening material 402-*a*, wherein the fastening materials are not yet engaged, shown in a side view. The male fastening material 401-*a* can be configured in the same way as the male fastening material 220 of FIG. 2, including any alternative embodiments. The female fastening material 402-*a* can be configured in the same way as the female fastening material 320 of FIG. 3, including any alternative embodiments.

In the embodiment of FIG. 4A, the fastening materials are parallel with each other, although this is not required. The fastening materials are spaced apart from each other. The male fastening elements of the male fastening material 401-*a* are facing inward, toward the female fastening material 402-*a*. FIG. 4A includes a horizontal direction 430, which is parallel with the planes of the fastening materials, as well as a vertical direction 435, which is perpendicular to the horizontal direction 430.

Figure 4B:
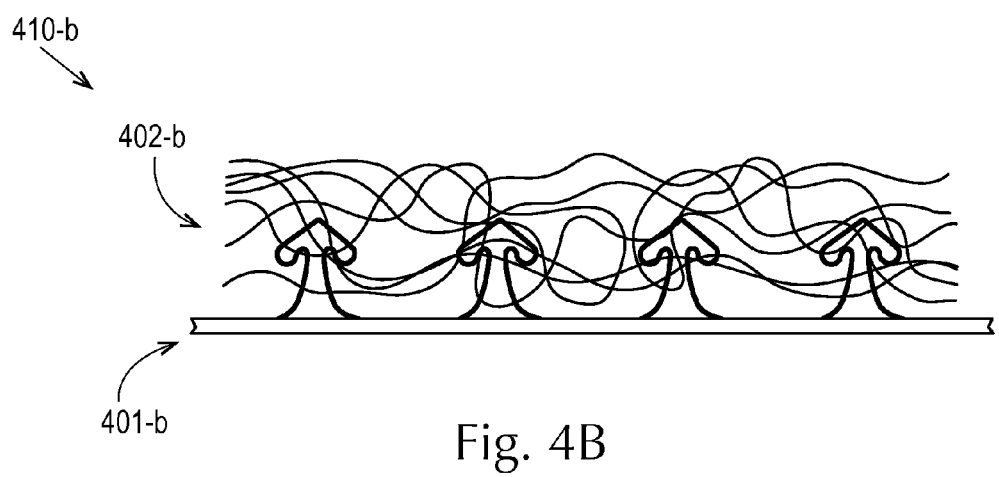
FIG. 4B is a representation of the computer based models of FIG. 4A in a subsequent state, after the fastening materials are engaged, shown in a side view.

FIG. 4B is a representation of a computer based model 410-*b*, which is the computer based model 410-*a* of FIG. 4A in a subsequent state, after the fastening materials are engaged, shown in a side view. FIG. 4B includes the horizontal direction 430, as well as the vertical direction 435. In the embodiment of FIG. 4B, the male fastening material 401-*b* has moved vertically into contact with the female fastening material 402-*b*, although this particular movement is not required for engagement. The fastening materials are not spaced apart from each other. The male fastening elements of the male fastening material 401-*b* are penetrating into the female fastening material 402-*b*, and at least one of the male fastening elements has captured at least one of the female fastening elements.

Figure 4C:
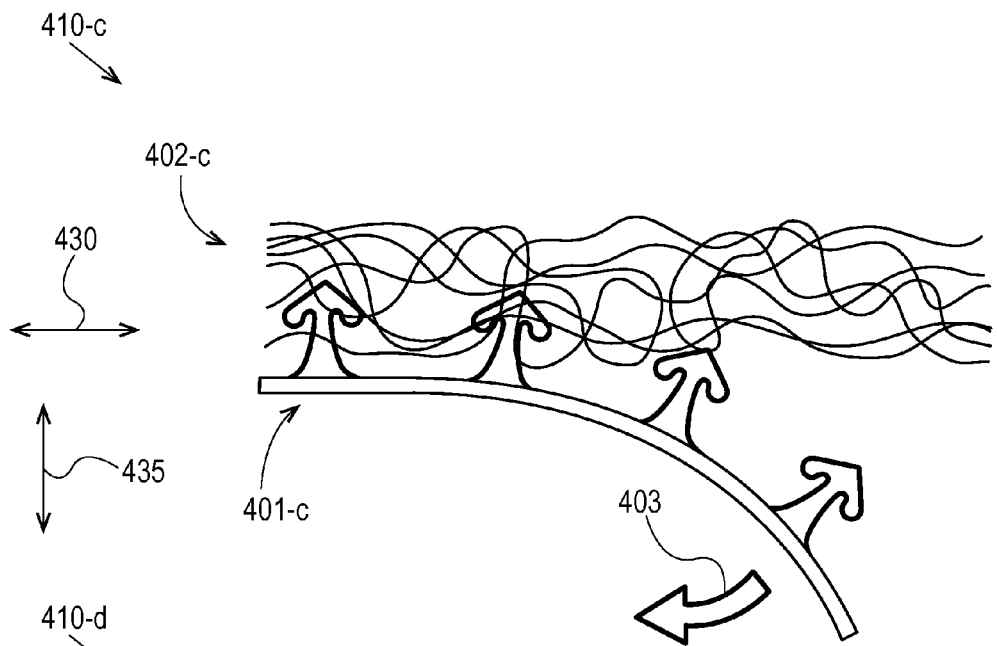
FIG. 4C is a representation of the computer based models of FIG. 4B in a subsequent state, while the male fastening material is being peeled away from the female fastening material.

FIG. 4C is a representation of the computer based model 410-*c*, which is the computer based model 410-*b* of FIG. 4B in a subsequent state, while the male fastening material 401-*c* is being peeled away from the female fastening material 402-*c*, while the female fastening material 402-*c* remains stationary. FIG. 4C includes the horizontal direction 430, as well as the vertical direction 435. The peeling of FIG. 4C can also be accomplished in alternative ways, including any manner described in the present disclosure.

Figure 4D:
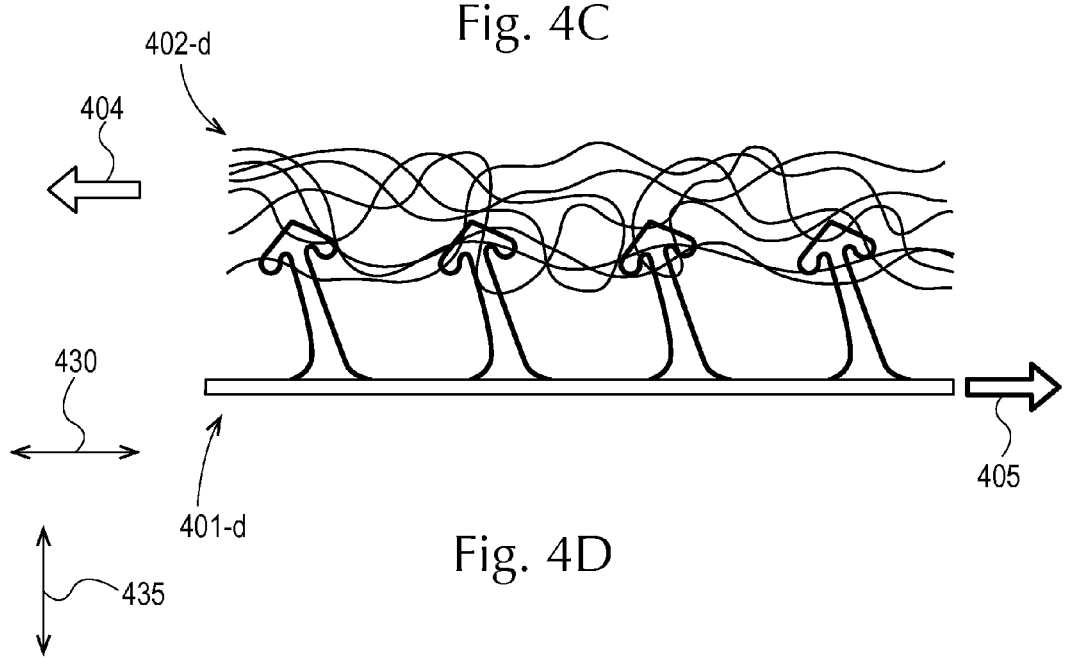
FIG. 4D is a representation of the computer based models of FIG. 4B in a subsequent state, while the fastening materials are being sheared with respect to each other.

FIG. 4D is a representation of the computer based model 410-*d*, which is the computer based model 410-*b* of FIG. 4B in a subsequent state, while the male fastening material 401-*d* and the female fastening material 402-*d* are being sheared with respect to each other. FIG. 4D includes the horizontal direction 430, as well as the vertical direction 435. The shearing of FIG. 4D can also be accomplished in alternative ways, including any manner described in the present disclosure.

Figure 4E:
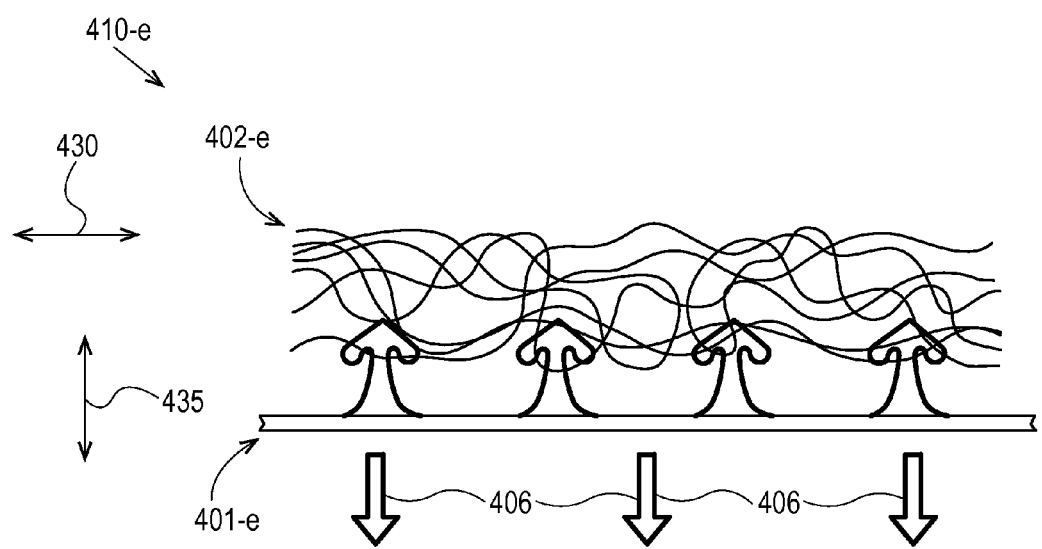
FIG. 4E is a representation of the computer based models of FIG. 4B in a subsequent state, while the fastening materials are being vertically pulled away from each other.

FIG. 4E is a representation of the computer based model 410-*e*, which is the computer based model 410-*b* of FIG. 4B in a subsequent state, while the male fastening material 401-*e* and the female fastening material 402-*e* are being vertically separated with respect to each other. FIG. 4E includes the horizontal direction 430, as well as the vertical direction 435. In FIG. 4C, the male fastening material 401-*e* is being pulled vertically 435 downward while the female fastening material 402-*e* remains stationary. However, in an alternate embodiment, the female fastening material 402-*e* can be pulled vertically 435 upward while the male fastening material 401-*e* remains stationary. In another alternate embodiment, the male fastening material 401-*e* can be pulled vertically 435 downward while the female fastening material 402-*e* can be pulled vertically 435 upward. Any of the vertical separations described in connection with the embodiments of FIG. 4E can be used to transform models of the engaged fastening materials, as described in the third step 103, and/or the fourth step 104, and/or the fifth step 105 of the method 100 of FIG. 1.

Figure 5A:
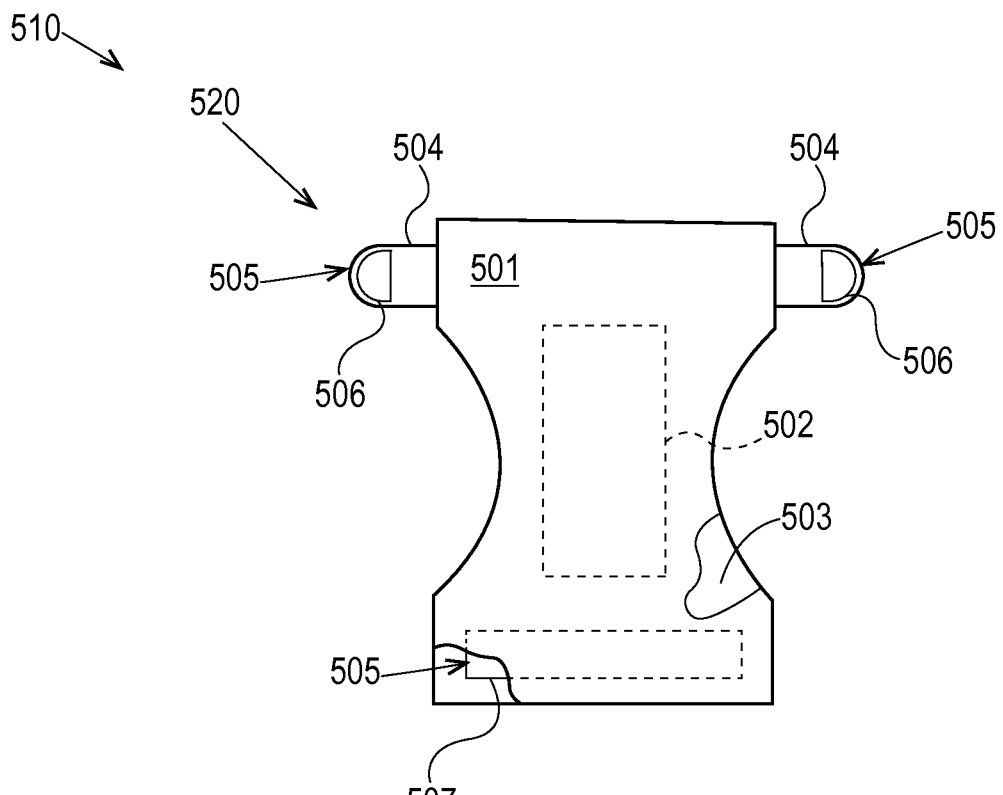
FIG. 5A is a representation of a computer based model of an exemplary front-fastenable disposable wearable absorbent article having a hook and loop fastening system, with the inside of the article shown.

FIG. 5A is a representation of a computer based model 510 of an exemplary front-fastenable disposable wearable absorbent article 520, having a hook and loop fastening system. However, embodiments of the present disclosure can use any kind of fastenable wearable absorbent article. FIG. 5A shows a top view of an inside of the article 520, laid out flat. The article 520 includes a topsheet 501, an outer cover 503, and an absorbent core 502 disposed between the topsheet 501 and the outer cover 503. In various embodiments, part, parts, or all of the outer cover 503 can be inextensible, or inelastically extensible, or elastically extensible, either laterally, or longitudinally, or both laterally and longitudinally. A portion of the topsheet 501 is illustrated as cut-away to show a portion of the outer cover 503. In the embodiment of FIG. 5A, the outer cover 503 has a fibrous outer surface. The article 520 includes side ears 504 attached to a back of the article 520. The article 520 also includes a hook and loop fastening system 505 for fastening the article 520 around a wearer. The hook and loop fastening system 505 includes a female fastening material 507 and pieces of a male fastening material 506. In the embodiment of FIG. 5A, the female fastening material 507 is a landing zone disposed on the outside of the front of the outer cover 503. A portion of the topsheet 501 is illustrated as cut-away to show a portion of the female fastening material 507. A piece of the male fastening material 506 is disposed on each of the side ears 504. In various embodiments, part, parts, or all of either or both of the side ears 504 can be inextensible, or inelastically extensible, or elastically extensible, either laterally, or longitudinally, or both laterally and longitudinally.

The disposable wearable absorbent article 520 can also be configured in various alternative embodiments. Any of the single pieces of fastening material on the article 520 may be replaced with two or more pieces of the fastening material. Any piece of either of the fastening materials may be integral with one or more other materials, layers, structures, or features, disclosed herein or known in the art, or to a chassis of the article 520. As an example, the male fastening material 506 may be integral with the side ear 504; that is, one or more materials of the side ear 504 may form the male fastening material. As another example, the female fastening material 507 may be integral with the outer cover 503; that is, one or more materials of the outer cover 503 may form the female fastening material.

The male fastening material 506 and the female fastening material 507 may be located in different locations; for example, the male fastening material 506 may be disposed on the outside of the front of the outer cover 503 and one or more pieces of the female fastening material 507 may be disposed on each of the side ears 504. The front-fastenable disposable wearable absorbent article 520 can alternatively be configured as a rear-fastenable disposable wearable absorbent article. A front-fastenable or rear-fastenable disposable wearable absorbent article can alternatively be configured to fasten only on one side. The front-fastenable disposable wearable absorbent article 520 can alternatively be configured with side margins, instead of side ears. The disposable wearable absorbent article 520 can alternatively be configured as a reusable wearable absorbent article, with a removable absorbent insert.

Also, the disposable wearable absorbent article 520, or any of its alternative embodiments, can be configured with another fastening system that includes one or more pieces of either or both of the male fastening material 506 and the female fastening material 507, including any of their alternative embodiments. For example, the disposable wearable absorbent article 520 can include a fastening system for attaching a removable absorbent insert to a chassis of the article 520. As another example, the disposable wearable absorbent article 520 can include a fastening system for attaching one or more materials, layers, structures, or features, disclosed herein or known in the art, to each other or to a chassis of the article 520.

Part, parts, or all of the female fastening material 507 can be configured in any manner disclosed herein or known in the art, including any workable combination of structures or features. For example, the female fastening material 507 can be configured in the same way as the female fastening material 320 of FIG. 3, including any alternative embodiments. Part, parts, or all of either or both pieces of the male fastening material 506 can be configured in any manner disclosed herein or known in the art, including any workable combination of structures or features. For example, the male fastening material 506 can be configured in the same way as the male fastening material 220 of FIG. 2, including any alternative embodiments.

Part, parts, or all of the fastening system 505 can be configured in any manner disclosed herein or known in the art, including any workable combination of structures or features. As an example, the fastening system 505 can include the male fastening material 506, as described above, but may include, a female fastening material that is configured differently than the female fastening material 507, and instead is configured as some other female fastening material known in the art. As another example, the fastening system 505 can include the female fastening material 507, as described above, but may include, a male fastening material that is configured differently than the male fastening material 506, and instead is configured as some other male fastening material known in the art.

Part, parts, or all of the front-fastenable disposable wearable absorbent article 520 can be configured in any manner disclosed herein or known in the art, including any workable combination of structures or features, including any alternative embodiments.

Figure 5B:
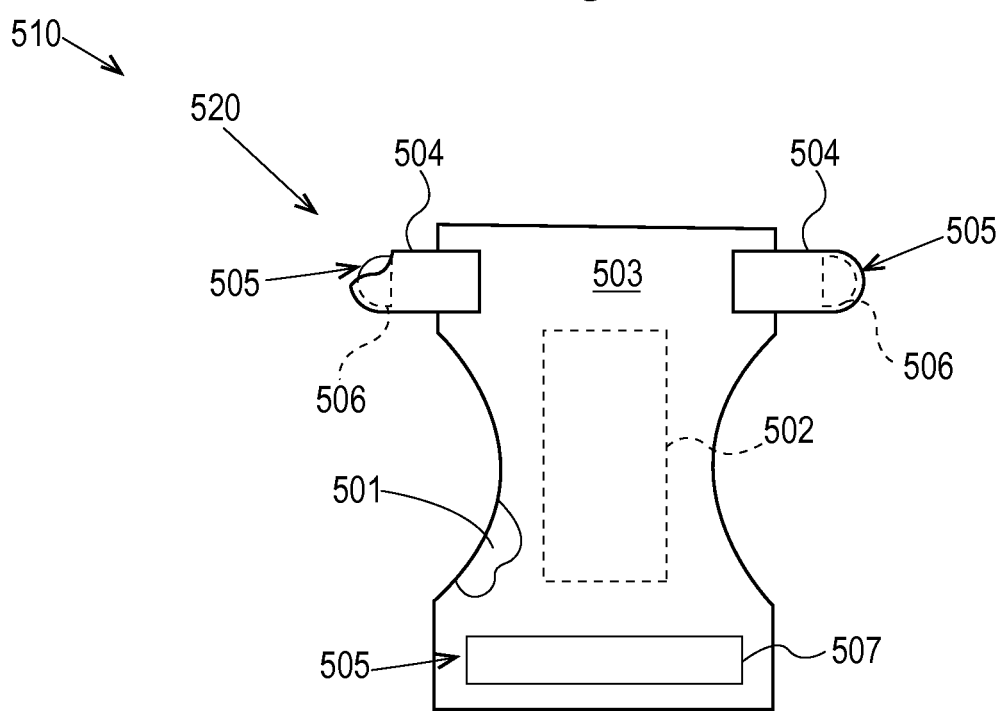
FIG. 5B is another representation of the computer based model of the front-fastenable disposable wearable absorbent article of FIG. 5A, with the outside shown.

FIG. 5B is another representation of the computer based model 510 of the front-fastenable disposable wearable absorbent article 520 of FIG. 5A. FIG. 5B shows a top view of an outside of the article 520, laid out flat. A portion of the outer cover 503 is illustrated as cut-away to show a portion of the topsheet 501. A portion of one of the side ears 504 is also illustrated as cut-away to show a portion of the male fastening material 506.

Any embodiment of the front-fastenable disposable wearable absorbent article 520 of FIGS. 5A and 5B can be manufactured with the fastening system 505 unfastened, or partially fastened, or fully fastened. Any embodiment of the front-fastenable disposable wearable absorbent article 520 of FIGS. 5A and 5B can be sold with the fastening system 505 unfastened, or partially fastened, or fully fastened. When an embodiment of the front-fastenable disposable wearable absorbent article 520 of FIGS. 5A and 5B is sold as unfastened or partially fastened, the consumer, user, or caregiver can fully fasten the article around a wearer.

Figure 6A:
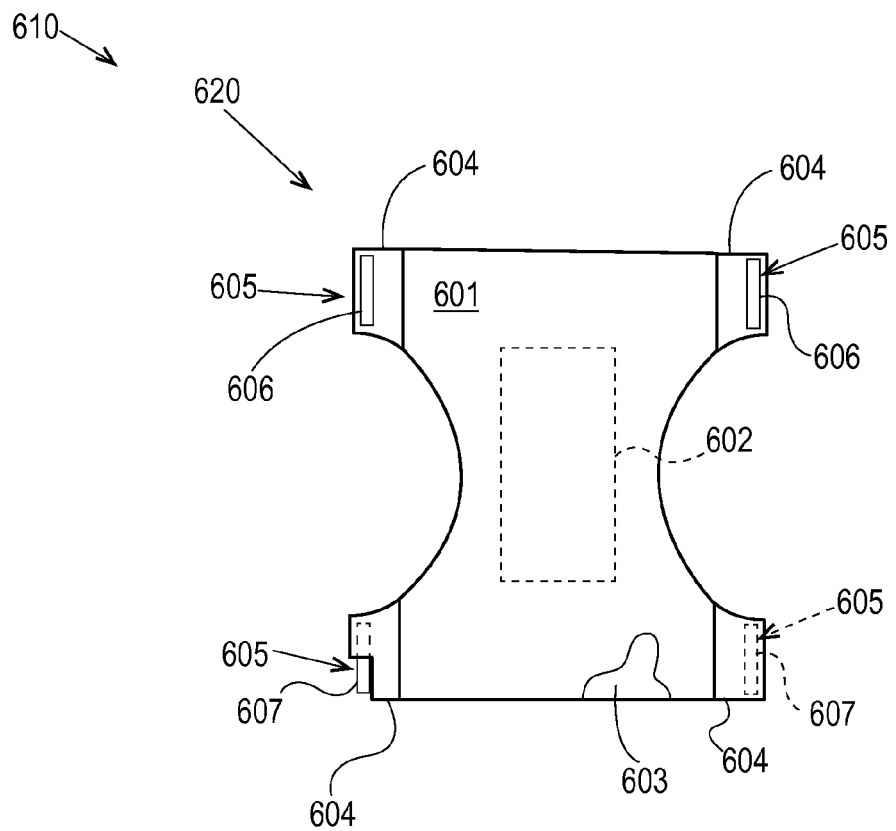
FIG. 6A is a representation of a computer based model of an exemplary side-fastenable disposable wearable absorbent article having a hook and loop fastening system, with the inside of the article shown.

FIG. 6A is a representation of a computer based model 610 of an exemplary side-fastenable disposable wearable absorbent article 620, having a hook and loop fastening system. However, embodiments of the present disclosure can use any kind of fastenable wearable absorbent article. FIG. 6A shows a top view of an inside of the article 620, laid out flat. The article 620 includes a topsheet 601, an outer cover 603, and an absorbent core 602 disposed between the topsheet 601 and the outer cover 603. In various embodiments, part, parts, or all of the outer cover 603 can be inextensible, or inelastically extensible, or elastically extensible, either laterally, or longitudinally, or both laterally and longitudinally. A portion of the topsheet 601 is illustrated as cut-away to show a portion of the outer cover 603. In the embodiment of FIG. 6A, the outer cover 603 has a fibrous outer surface. The article 620 includes side panels 604 attached to both sides of the front of the article 620 and to both sides of the back of the article 620. The article 620 also includes a hook and loop fastening system 605 for fastening the article 620 around a wearer. The hook and loop fastening system 605 includes pieces of a male fastening material 606 and pieces of a female fastening material 607. In the embodiment of FIG. 6A, a piece of the male fastening material 606 is disposed on the inside of each of the side ears 604 in the back of the article 620, and a piece of the female fastening material 607 is disposed on the outside of each of the side ears 604 in the front of the article 620. A portion of one of the side panels 604 is illustrated as cut-away to show a portion of one of the pieces of the female fastening material 607. In various embodiments, part, parts, or all of either or both of the side panels 604 can be inextensible, or inelastically extensible, or elastically extensible, either laterally, or longitudinally, or both laterally and longitudinally.

The disposable wearable absorbent article 620 can also be configured in various alternative embodiments. Any of the single pieces of fastening material on the article 620 may be replaced with two or more pieces of the fastening material. Any piece of either of the fastening materials may be integral with one or more other materials, layers, structures, or features, disclosed herein or known in the art, or to a chassis of the article 620. As examples, the male fastening material 606 and/or the female fastening material 607 may be integral with the side ears 604; that is, one or more materials of the side ear 604 may form the fastening material.

The male fastening material 606 and the female fastening material 607 may be located in different locations. For example, the male fastening material 606 may be disposed on either or both of the side panels 604 in the front of the article and the female fastening material 607 may be disposed on either or both of the side panels 604 in the back of the article 620. As another example, one or more pieces of the male fastening material 606 may be disposed on the outside of one or more of the side panels 604 while one or more pieces of the female fastening material 607 may be disposed on the inside of one or more of the side panels 604.

The side-fastenable disposable wearable absorbent article 620 can alternatively be configured with side panels only in the front, or only in the back, or only on one side. The side-fastenable disposable wearable absorbent article 620 can alternatively be configured with side margins, instead of side panels. The side-fastenable disposable wearable absorbent article 620 can alternatively be configured without discrete side panels, but with one or more pieces of fastening material disposed on either or both sides of the chassis in the front or the back of the article 620. The disposable wearable absorbent article 620 can alternatively be configured as a reusable wearable absorbent article, with a removable absorbent insert.

Also, the disposable wearable absorbent article 620, or any of its alternative embodiments, can be configured with another fastening system that includes one or more pieces of either or both of the male fastening material 506 and the female fastening material 507, including any of their alternative embodiments. For example, the disposable wearable absorbent article 620 can include a fastening system for attaching a removable absorbent insert to a chassis of the article 620. As another example, the disposable wearable absorbent article 620 can include a fastening system for attaching one or more materials, layers, structures, or features, disclosed herein or known in the art, to each other or to a chassis of the article 620.

Part, parts, or all of either piece or both pieces of the female fastening material 607 can be configured in any manner disclosed herein or known in the art, including any workable combination of structures or features. For example, the female fastening material 607 can be configured in the same way as the female fastening material 320 of FIG. 3, including any alternative embodiments. Part, parts, or all of either piece or both pieces of the male fastening material 606 can be configured in any manner disclosed herein or known in the art, including any workable combination of structures or features. For example, the male fastening material 606 can be configured in the same way as the male fastening material 220 of FIG. 2, including any alternative embodiments.

Part, parts, or all of the side-fasteable disposable wearable absorbent article 620 can be configured in any manner disclosed herein or known in the art, including any workable combination of structures or features, including any alternative embodiments.

Figure 6B:
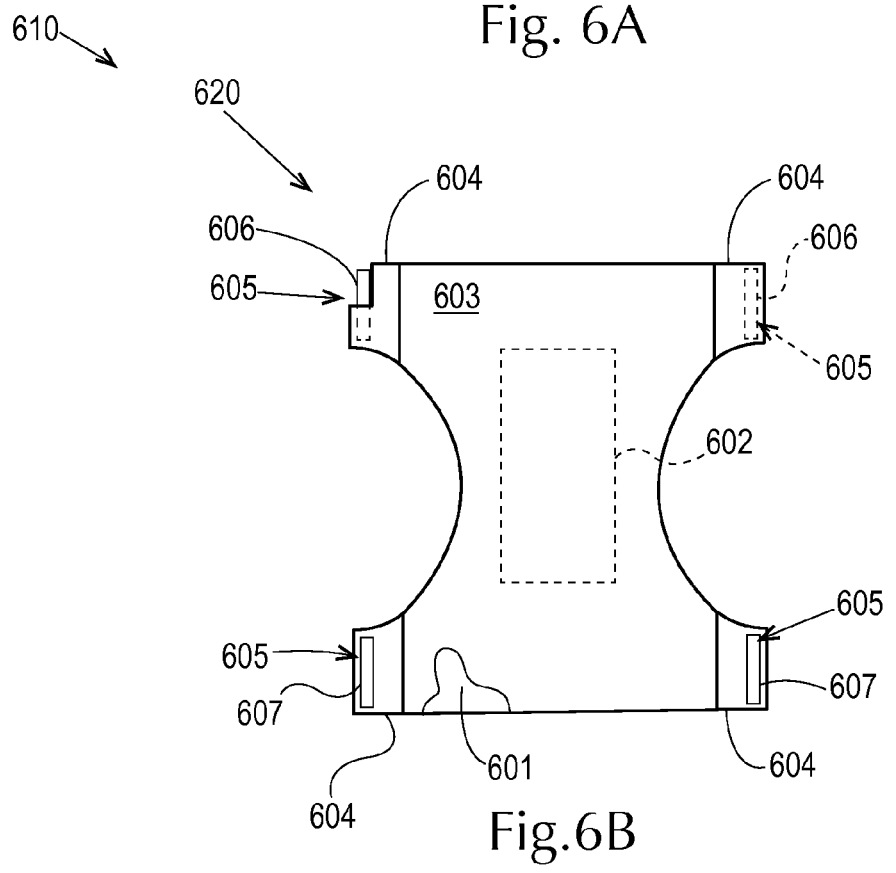
FIG. 6B is another representation of the computer based model of the side-fastenable disposable wearable absorbent article of FIG. 6A, with the outside shown.

FIG. 6B is another representation of the computer based model 610 of the side-fasteable disposable wearable absorbent article 620 of FIG. 6A. FIG. 6B shows a top view of an outside of the article 620, laid out flat. A portion of the outer cover 603 is illustrated as cut-away to show a portion of the topsheet 601. A portion of one of the side panels 604 is also illustrated as cut-away to show a portion of one of the pieces of the male fastening material 606.

Any embodiment of the side-fasteable disposable wearable absorbent article 620 of FIGS. 6A and 6B can be manufactured with the fastening system 605 unfastened, or partially fastened, or fully fastened. Any embodiment of the front-fasteable disposable wearable absorbent article 620 of FIGS. 6A and 6B can be sold with the fastening system 605 unfastened, or partially fastened, or fully fastened. When an embodiment of the front-fasteable disposable wearable absorbent article 620 of FIGS. 6A and 6B is sold as unfastened or partially fastened, the consumer, user, or caregiver can fully fasten the article around a wearer.

Any of the wearable absorbent articles disclosed herein can be configured with various structures and/or features, as will be understood by one of skill in the art. As an example, a wearable absorbent article can include any of the following layers (from the skin of the wearer outward): a topsheet, an acquisition layer, a distribution layer, a core cover, a storage layer, a dusting layer, and/or an outer cover, and/or one or more other layers known in the art, with each layer configured in any way known in the art. A layer in a wearable absorbent article can be formed from one or more of various materials, such as fibrous web, film, paper, tissue, etc. and laminates made from any combination of any of these, in any way known in the art. Each layer in a wearable absorbent article can be configured with various appropriate properties, such as hydrophillicity, hydrophobicity, liquid permeability, liquid impermeability, porosity, breathability, extensibility, elasticity, opacity, transparency, strength, and/or softness, etc. in any way known in the art.

An absorbent core can include one or more absorbent materials, such as superabsorbent materials and/or natural materials (which may or may not be processed into various forms). In various embodiments, part, parts, or all of a topsheet, an acquisition layer, a distribution layer, a core cover, a storage layer, and/or a dusting layer can include various coatings and/or additives such as lotions, perfumes, and sensates for various purposes, such as antimicrobial action, deodorizing, promoting skin health, etc. An absorbent core can be configured as a bucket-shaped absorbent core, as part of a removable absorbent core, as part of a replaceable absorbent core, as part of an absorbent core assembly, etc.

Also, a disposable wearable absorbent article can include any of the following: a waist band, a finished waist edge, a leg band, a finished leg opening, an outer leg cuff, an inner leg cuff, and/or a barrier leg cuff. Further, a disposable wearable absorbent article can include any of the following: a feces containment compartment, one or more wetness indicators, disposal tapes, etc. Still further, various structures and features of a disposable wearable absorbent article can include artwork, passive graphics, active graphics, indicia, and product information, in any combination known in the art.

A computer based model of an absorbent article, such as computer based models of absorbent articles 510 and 610 of FIGS. 5A-6B can be created as described below. A computer based model that represents an absorbent article can be created by providing dimensions and material properties to modeling software and by generating a mesh for the article using meshing software.

A computer based model of an absorbent article can be created with dimensions that are similar to or the same as dimensions that represent parts of a real world absorbent article. These dimensions can be determined by measuring actual samples, by using known values, or by estimating values. Alternatively, a model of an absorbent article can be configured with dimensions that do not represent a real world absorbent article. For example, a model of an absorbent article can represent a new variation of a real world absorbent article or can represent an entirely new absorbent article. In these examples, dimensions for the model can be determined by varying actual or known values, by estimating values, or by generating new values. The model can be created by putting values for the dimensions of parts of the absorbent article into the modeling software.

The computer based model of the absorbent article can be created with material properties that are similar to or the same as material properties that represent a real world absorbent article. These material properties can be determined by measuring actual samples, by using known values, or by estimating values. Alternatively, a model of an absorbent article can be configured with material properties that do not represent a real world absorbent article. For example, a model of an absorbent article can represent a new variation of a real world absorbent article or can represent an entirely new absorbent article. In these examples, material properties for the model can be determined by varying actual or known values, by estimating values, or by generating new values.

The computer based model of the absorbent article can be created with a mesh for the parts of the article. A mesh is a collection of small, connected polygon shapes that define the set of discrete elements in a CAE computer based model. The type of mesh and/or the size of elements can be controlled with user inputs into the meshing software, as will be understood by one of ordinary skill in the art.

Embodiments of the present disclosure can at least assist in predicting whether or not particular male fastening materials and/or particular female fastening materials can be used to form reliable hook and loop fastening systems. The present disclosure includes methods of simulating the physical behavior of hook and loop fastening systems. As a result, fastening materials, fastening systems, and articles with fastening systems can be evaluated and modified as computer based models before they are tested as real world things.

A computer based model of a hook and loop fastening system can be easily varied, to determine how such variations affect the fastening performance of the system. In some embodiments, a computer based model of a hook and loop fastening system can be systematically varied in a virtual design of experiments that tests many variations of several aspects of the model. The empirical results of the virtual experiments can be statistically analyzed to determine the relationship between the variations and the fastening performance of the system.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method comprising:
   representing a male fastening material having a plurality of male fastening elements, with a computer based model of the male fastening material;
   representing a female fastening material having a plurality of female fastening elements, with a computer based model of the female fastening material;
   transforming the computer based models of the fastening materials, by engaging the model of the male fastening material with the model of the female fastening material, to form engaged fastening materials; and
   representing the transformed fastening materials with a computer based model of the engaged fastening materials.

2. The method of claim 1, wherein the representing of the male fastening material includes representing a male fastening material, wherein each male fastening element has an overall height that is less than or equal to 1000 micrometers, and the male fastening material has an element density of at least 10 male fastening elements per square centimeter.

3. The method of claim 1, wherein the representing of the female fastening material includes representing a female fastening material, wherein the female fastening material is a three-dimensional fibrous material, wherein the female fastening elements are fiber loops of the fibrous material, wherein each fiber loop has a fiber cross-section with an overall dimension that is less than or equal to 100 micrometers.

4. The method of claim 1, wherein the transforming includes engaging by moving one of the models of fastening material into contact with the other model of fastening material, while the other model of fastening material remains stationary with respect to the one model of fastening material.

5. The method of claim 1, wherein the transforming includes engaging by moving at least one of the models of fastening material, only vertically with respect to the other model of fastening material.

6. The method of claim 1, wherein the transforming includes engaging by moving at least one of the models of fastening material, only horizontally with respect to the other model of fastening material.

7. The method of claim 1, wherein the transforming includes engaging by:
   moving at least one of the models of fastening material, vertically with respect to the other model of fastening material; and
   moving at least one of the models of fastening material, horizontally with respect to the other model of fastening material.

8. The method of claim 1, wherein the transforming includes deforming at least some of the male fastening elements during the engaging.

9. The method of claim 1, wherein the transforming includes deforming at least some of the female fastening elements during the engaging.

10. The method of claim 1, comprising further transforming the computer based models of the engaged fastening materials, by applying only a peel boundary condition to one of the models of engaged fastening material, with respect to the other model of engaged fastening material.

11. The method of claim 10, wherein the transforming includes deforming at least some of the male fastening elements while applying the peel boundary condition.

12. The method of claim 10, wherein the further transforming includes breaking at least some of the male fastening elements while applying the peel boundary condition.

13. The method of claim 10, wherein the transforming includes deforming at least some of the female fastening elements while applying the peel boundary condition.

14. The method of claim 10, wherein the further transforming includes breaking at least some of the female fastening elements while applying the peel boundary condition.

15. The method of claim 1, comprising further transforming the computer based models of the engaged fastening materials, by applying only a shear boundary condition to one of the models of engaged fastening material, with respect to the other model of engaged fastening material.

16. The method of claim 15, wherein the transforming includes deforming at least some of the male fastening elements while applying the shear boundary condition.

17. The method of claim 15, wherein the further transforming includes breaking at least some of the male fastening elements while applying the shear boundary condition.

18. The method of claim 15, wherein the transforming includes deforming at least some of the female fastening elements while applying the shear boundary condition.

19. The method of claim 15, wherein the further transforming includes breaking at least some of the female fastening elements while applying the shear boundary condition.

20. The method of claim 1, comprising further transforming the computer based models of the engaged fastening materials, by:
   applying a peel boundary condition to one of the models of engaged fastening material, with respect to the other model of engaged fastening material; and applying a shear boundary condition to one of the models of engaged fastening material, with respect to the other model of engaged fastening material.

21. The method of claim 1, comprising:
further transforming the computer based models of the engaged fastening materials, by at least partially disengaging the model of the male fastening material from the model of the female fastening material, to form at least partially disengaged fastening materials; and
representing the further transformed fastening materials with a computer based model of the at least partially disengaged fastening materials.

22. The method of claim 21, wherein the further transforming includes disengaging by only applying a peel boundary condition to one of the models of the fastening material, with respect to the other model of fastening material.

23. The method of claim 21, wherein the further transforming includes disengaging by only applying a shear boundary condition to one of the models of the fastening materials, with respect to the other model of fastening material.

24. The method of claim 21, wherein the transforming includes disengaging by:
applying a peel boundary condition to at least one of the models of fastening material, with respect to the other model of fastening material; and
applying a shear boundary condition to at least one of the models of fastening material, with respect to the other model of fastening material.

25. The method of claim 21, wherein the transforming includes deforming at least some of the male fastening elements during the at least partial disengaging.

26. The method of claim 21, wherein the further transforming includes breaking at least some of the male fastening elements during the at least partial disengaging.

27. The method of claim 21, wherein the transforming includes deforming at least some of the female fastening elements during the at least partial disengaging.

28. The method of claim 21, wherein the further transforming includes breaking at least some of the female fastening elements during the at least partial disengaging.

29. The method of claim 21, wherein:
the further transforming of the computer based models of the engaged fastening materials, includes fully disengaging the model of the male fastening material from the model of the female fastening material, to form a disengaged male fastening material and a disengaged female fastening material; and
representing the further transformed fastening materials with a computer based model of the fully disengaged fastening materials.

30. The method of claim 29, wherein the transforming includes deforming at least some of the male fastening elements during the full disengaging.

31. The method of claim 29, wherein the further transforming includes breaking at least some of the male fastening elements during the full disengaging.

32. The method of claim 29, wherein the transforming includes deforming at least some of the female fastening elements during the full disengaging.

33. The method of claim 29, wherein the further transforming includes breaking at least some of the female fastening elements during the full disengaging.

34. The method of claim 29, comprising:
further transforming the computer based models of the fastening materials, by re-engaging the model of the male fastening material with the model of the female fastening material, to form re-engaged fastening materials; and
representing the transformed fastening materials with a computer based model of the re-engaged fastening materials.

35. The method of claim 1, wherein the representing of the male fastening material includes representing the male fastening material, which has a defined size and a particular shape representing a size and a shape of a discrete piece of male fastening material in a hook and loop fastening system.

36. The method of claim 1, wherein the representing of the female fastening material includes representing the female fastening material, which has a defined size and a particular shape representing a size and a shape of a discrete piece of female fastening material in the hook and loop fastening system.

37. The method of claim 1, comprising representing at least part of an article that includes the hook and loop fastening system with a computer based model of the article, wherein the at least part of the article includes a first portion to which the male fastening material is joined, and the article includes a second portion to which the female fastening material is joined.

38. The method of claim 37, comprising representing the at least part of the article, wherein the article is a wearable article.

39. The method of claim 37, comprising representing the at least part of the article, wherein the article is a disposable wearable absorbent article.

40. The method of claim 39, comprising representing substantially all of the disposable wearable absorbent article.

41. A computer readable medium having instructions for causing a device to perform a method, the method comprising:
representing a male fastening material having a plurality of male fastening elements, with a computer based model of the male fastening material;
representing a female fastening material having a plurality of female fastening elements, with a computer based model of the female fastening material;
transforming the computer based models of the fastening materials, by engaging the model of the male fastening material with the model of the female fastening material, to form engaged fastening materials; and
representing the transformed fastening materials with a computer based model of the engaged fastening materials.

* * * * *